(12) United States Patent
Hwang et al.

(10) Patent No.: US 6,420,519 B1
(45) Date of Patent: Jul. 16, 2002

(54) MODIFYING TISSUE SURFACES BY LIQUID CRYSTAL FORMATION

(75) Inventors: Julia Hwang; Samuel I. Stupp, both of Evanston, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/446,966

(22) PCT Filed: Jul. 21, 1998

(86) PCT No.: PCT/US98/15244

§ 371 (c)(1),
(2), (4) Date: Dec. 29, 1999

(87) PCT Pub. No.: WO99/03419

PCT Pub. Date: Jan. 28, 1999

Related U.S. Application Data

(60) Provisional application No. 60/053,301, filed on Jul. 21, 1997.

(51) Int. Cl.[7] .................. A61B 19/00; A61K 38/00; C07K 14/00
(52) U.S. Cl. ................. 530/324; 128/898; 424/422; 424/423; 424/424; 424/425; 424/426; 514/2; 514/944; 514/953; 514/965; 623/11; 623/13; 623/16; 623/18; 530/300; 530/324; 521/60; 528/328
(58) Field of Search .................. 530/300, 324; 521/60; 528/328; 424/423, 422, 424, 425, 426; 623/13, 11, 16, 18; 514/2, 944, 953, 965; 128/898

(56) References Cited

U.S. PATENT DOCUMENTS

| | | |
|---|---|---|
| 4,141,973 A | 2/1979 | Balazs .................. 424/180 |
| 4,846,835 A | 7/1989 | Grande .................. 623/11 |
| 5,206,023 A | 4/1993 | Hunzicker .................. 424/423 |
| 5,655,546 A | 8/1997 | Halpern et al. .................. 128/898 |

OTHER PUBLICATIONS

Swann, "Macromolecules of Synovial," *The Joints and Synovial Fluid*, vol. 1. Academic Press: New York, pp. 407–432, 1978.

Freed et al., "Neocartilage Formation in vitro and in vivo Using Cells Cultured on Synthetic Biodegradable Polymers," *J. Biomedical Materials Research*, vol. 27, pp. 11–13, 1993.

Balazs, "The Physical Properties of Synovial Fluid and the Special Role of Hyaluronic Acid," *Disorders of the Knee*, second edition, 1974, Arthur J. Helfet, J.B. Lippincott.

Bazuin, C.G. and Tork, "Materials From Non–liquid Crystalline," *Macromolecules*, vol. 28, pp. 8877–8880, 1995.

Hills, "Synovial Surfactant and the Hydrophobic Articular Surface," *J. of Rheumatology*, vol. 23, pp. 1323–1325, 1996.

Jugensen et al. "A New Biological Glue for Cartilage–Cartilage Interfaces: Tissue Transglutaminase," *J. of Bone and Joint Surgery*, vol. 70–A, Feb. 1997, pp. 185–193.

Caceci "Connective Tissues III: Cartilage" Lab Exercises, Royal (Dick) School of Veterinary Studies, 1997.

Primary Examiner—Karen Cochrane Carlson
Assistant Examiner—Chih-Min Kam
(74) Attorney, Agent, or Firm—Barnes & Thornburg

(57) ABSTRACT

A method for modifying the surface properties of tissue in vivo is described. The method comprises forming a liquid crystalline matrix on the tissue surface by contacting the surface with a composition comprising a poly(hydroxy substituted amino acid). Compositions comprising a poly(hydroxy substituted amino acid) and synovial fluid are also provided.

14 Claims, 1 Drawing Sheet

MODIFYING TISSUE SURFACES BY LIQUID CRYSTAL FORMATION

CROSS-REFERENCES TO RELATED APPLICATIONS

Figure 1:
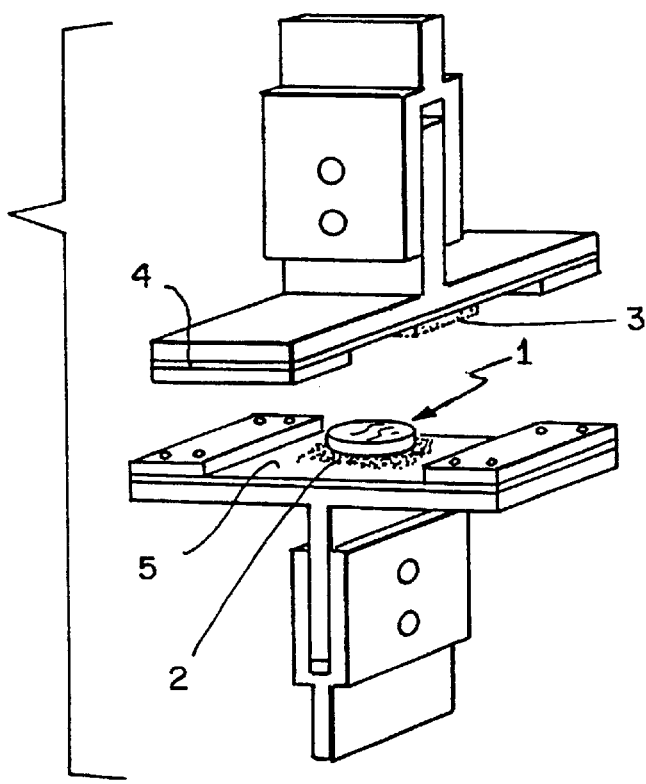

This application is a U.S. national application of international application Ser. No. PCT/US98/15244 filed Jul. 21, 1998, which claims priority to U.S. provisional application Ser. No. 60/053,301 filed Jul. 21, 1997.

FIELD OF THE INVENTION

This invention relates to a method of modifying the surface properties of tissue by forming on the tissue surface liquid crystalline matrices comprising components of the tissue or of biological fluids wetting the tissue surface. More particularly, in one embodiment, this invention is directed to forming a liquid crystalline matrix comprising synovial fluid on a cartilage surface by contacting such surfaces with a poly(hydroxy substituted amino acid) to improve bonding of surgical glues to the cartilage surface.

BACKGROUND AND SUMMARY OF THE INVENTION

Damage to articular cartilage results in significant disability to many people, young and old alike. Damaged articular cartilage has very limited capacity to repair itself and restore normal function. The repair tissue that is formed in response to damaged articular cartilage is often in the form of fibrocartilage, which does not have the load-bearing capacity of the original articular cartilage. Also fibrocartilage does not exhibit the lubricating ability as does hyaline or articular cartilage. Over time this leads to further destruction of the cartilage and eventually to osteoarthritis. For older patients, one solution to this problem is total joint replacement. However, for younger patients who suffer from cartilage defects and lesions, another form of treatment is needed.

Reconstructive orthopaedic surgery is becoming increasingly necessary to treat patients with damaged cartilage deriving from congenital abnormalities or trauma. Current therapies include transplantation or allografts, implantation of artificial prosthetic devices, and neo-cartilage formation utilizing isolated chondrocytes in an organic support matrix or scaffold. However, each of those methods for repairing damaged cartilage has associated risks. In addition to complications by infection and host versus graft rejection, there is a high incidence of incomplete or disrupted bonding at the host-implant interface. Problems with adhesive bonding are particularly predominant, for example, at articular cartilage joints where the bonded surfaces are continuously bathed in synovial fluid. Hydration/lubrication of cartilage surfaces by synovial fluid is one of the major causes of problems associated with adhesive bonding to such surfaces.

A variety of adhesives or surgical glues has been studied for repair of cartilage and other tissue surfaces. Bioerodable adhesives may include fibrin-based materials, poly(amino acids), and designed polypeptides.

When the implant includes a polymer matrix, the polymer matrix can be glued to damaged cartilage to provide a bonded porous three-dimensional scaffold that can serve as a support for bioactive materials and for growth of chondrocyte cell populations. The scaffold serves as a template to help define the shape of the new tissue as it is being regenerated. If the synthetic material is a bioerodable or biodegradable polymer, the scaffold gradually degrades into natural metabolites which are removed from the defect site. Optimally, the repair tissue strongly resembles and functions as that of native cartilage.

The success of such treatment for repair of damaged cartilage depends in part on the ability of the surgical glue to bond to and stabilize the implant, transplant or polymer scaffold to the defect site. One characteristic of normal articular surfaces is its hydrophobicity. The hydrophobic cartilage surface comprises a phospholipid layer that provides lubricity for articulating cartilage surfaces in a normal joint. Unfortunately the same hydrophobic character of the articular surfaces which provides the low-friction interface also reduces the effectiveness of surgical glues to form a strong bond between native cartilage and implanted repair material. Hydrophobic components on the surface interfere with the adhesion of surgical glues to the cartilage surface, and it has been found that they are difficult to remove from the cartilage surface to improve surface bonding.

In addition to the hydrophobic character of cartilage surfaces, the synovial fluid which continuously bathes joint tissues also interferes with the bonding of joint tissues using conventional surgical adhesives/glues. In vivo synovial fluid continuously wets the surfaces of articular joints and the associated cartilage, tendon and ligament surfaces. Synovial fluid appears to have two main functions: the lubrication and nutrition of the joint tissues. Synovial fluid is comprised of a complex mixture of macromolecular constituents including components derived from the blood, substances secreted by the joint tissues, and products derived from catabolism of the joint. One of the main constituents of synovial fluid is hyaluronic acid. Hyaluronic acid is a polyacidic polysaccharide. In the joint surfaces, hyaluronic acid is believed to interact with proteoglycans to form large aggregates collectively providing a homogeneous matrix on articular cartilage surfaces. In the proteoglycan matrix, hyaluronic acid is covalently bound to polypeptides comprising keratin sulfate and chondroitin sulfate chains via smaller linker proteins. The proteoglycan matrix can be repeatedly compressed and still return to its original shape after being deformed. The matrix helps cushion the compressive forces on articular cartilage surfaces.

The biological components existing in vivo on cartilage surfaces and in articular joints work to prevent or diminish the effectiveness of surgical glues to bind and stabilize transplants of native cartilage or implants of synthetic material to cartilage surfaces in need of repair. There is need to improve the effectiveness of surgical glues to bond cartilage surfaces in connection with surgical reconstruction or repair of joint structures.

One embodiment of the present invention addresses that need. It is based in part on the discovery that cartilage surfaces wet with synovial fluid can be treated with a composition comprising a poly(hydroxy substituted amino acid) to enhance the bonding of the cartilage surface with surgical adhesives/glues. It has been found that synovial fluid forms a liquid crystalline composition when combined with poly(hydroxy substituted amino acids). The synovial fluid appears to exhibit a greater affinity for the added polypeptide than for cartilage components, thus resulting in modification of the cartilage surface characteristics. Complexing the synovial fluid associated with the cartilage surface to form the gelatinous liquid crystalline matrix increases the effectiveness of glue or cement to bind the cartilage surface. Optionally the gelled matrix can be separated from the cartilage, prior to application of the surgical glue to further improve bonding of the surface with surgical glues.

Thus, one aspect the present invention relates to a novel liquid crystalline composition comprising a poly(hydroxy substituted amino acid) and synovial fluid.

Another aspect of this invention relates to an improved method of preparing a cartilage surface to enhance the efficacy of surgical glues to bind to the cartilage surface.

Yet another aspect of this invention is an improved method of removing synovial fluid from cartilage surfaces and articular cartilage joints by contacting the cartilage surface (wetted with synovial fluid) with a poly(hydroxy substituted amino acid) to form a liquid crystalline matrix that can be readily removed from the cartilage surface.

In another embodiment of the invention, there is provided a more general method of modifying the surface characteristics of tissue in vivo by forming a liquid crystalline or mesomorphic matrix on said surface wherein the matrix comprises a component of the tissue surface or a component of a fluid wetting the tissue surface. The matrix can optionally be removed to provide a surface having a reduced amount of said component.

DETAILED DESCRIPTION OF THE INVENTION

One aspect of the present invention is an improved method of bonding adhesives or surgical glues to tissue surfaces in vivo. As used herein a surgical glue is an adhesive that is used during surgery to repair tissue that had been damaged because of injury or disease. An adhesive as used herein is a general term refering to any substance that bonds two surfaces together by adhering to the surface of each.

The presence of synovial fluid on cartilage surfaces reduces the effectiveness of surgical glues to bond to the cartilage surfaces. Contacting the surface with a composition comprising a poly(hydroxy substituted amino acid) to form a gelled (liquid crystalline or mesomorphic) synovial fluid complex/matrix works to reduce the interference of synovial fluid with the bonding of surgical glues to cartilage surfaces and surfaces of other tissues wetted with synovial fluid.

In one preferred embodiment the liquid crystalline matrix is formed by contacting the cartilage surface with polythreonine. A gelatinous matrix forms immediately when an aqueous solution polythreonine is added to synovial fluid. Observation of the gelatinous matrix under an optical microscope with polarized light reveals that the matrix is birefringent, indicating formation of a liquid crystalline matrix.

The interaction between the poly(hydroxy substituted amino acid) polythreonine and synovial fluid is believed to be due to hydrogen bonding and other polypeptides of similar structure and functionality may be used. Thus, for example, polypeptides which are a homopolymer, a copolymer or a terpolymer of hydroxy substituted amino acids, particularly those having a molecular weight of about 3,000 to about 100,000 Daltons, more preferably about 5,000 to about 50,000 Daltons, may promote the formation of a gelatinous synovial fluid complex. Suitable poly(hydroxy substituted amino acid) homopolymers include polythreonine, polyserine, polytyrosine, poly(hydroxyproline), and poly-5-hydroxy lysine. Polymers of L-amino acids are preferred. Polypeptides comprising copolymers, terpolymers and block copolymers of hydroxy substituted amino acids may also be suitable for use in accordance with this invention. In one embodiment the poly(hydroxy substituted amino acid) comprises polythreonine, e.g., a homopolymer of threonine or a polythreonine block copolymer with other amino acids, including but not limited to hydroxy substituted amino acids.

The method by which the polypeptide and the synovial fluid are combined is not critical to the formation of the matrix. The matrix is formed by the addition of a poly(hydroxy substituted amino acid) to synovial fluid either as a solid or in an aqueous solution. Aqueous solutions of the poly(amino acid) are readily miscible with the synovial fluid. Where a solution of polythreonine is used, the gelatinous matrix forms upon the addition of the polythreonine solution at a concentration of about 5 mg to about 60 mg of polythreonine in 1 ml of water. Preferably the polythreonine concentration is about 50 mg per 1 ml of water. When solid polythreonine is added to synovial fluid with stirring, a gelatinous matrix forms almost immediately.

In another embodiment of the present invention, a composition comprising polythreonine or another effective poly(hydroxy substituted amino acid) is contacted with a synovial fluid wetted cartilage surface. The resulting matrix formed on the cartilage surface does not need to be separated from the cartilage to increase the efficacy of surgical glues. The presence of the gelatinous matrix at the articular cartilage joint is believed to impede further hydration or wetting of the cartilage surface by synovial fluid. Hydration/wetting of the surface by synovial fluid is known to increase the incidences of surgical glue breakdown on cartilage surfaces. Thus when treated in accordance with this invention, cartilage presents a surface which promotes more effective bonding with surgical glues than cartilage surfaces which have been prepared by methods currently known in the art.

In yet another embodiment of the invention, the gelatinous matrix formed on treatment of the synovial fluid wetted cartilage surface may be separated from the cartilage by methods known in the art to provide a cartilage surface which exhibits excellent bonding with surgical glues. The gel can be simply wiped from the surface with gauze or scraped from the surface. The articular cartilage surface can be initially cleaned of synovial fluid residue by the methods known in the art to remove a majority of the synovial fluid prior to the treatment in accordance with this invention. Despite the methods utilized to clean the cartilage, a remnant of synovial fluid remains on the surface and in the cartilage tissue. The residual synovial fluid can be gelled in accordance with this invention and then be removed to provide a cartilage surface essentially free of synovial fluid.

Removal of synovial fluid from the joint surface by blotting or wiping with sterile gauze is more effective after the addition of the poly(hydroxy substituted amino acid). Not only does the complexing poly(hydroxy substituted amino acid) incorporate the synovial fluid on the cartilage surface, but it also appears to extract at least a portion of the synovial fluid from the tissue at the surface of the cartilage. When the gel matrix is separated from the cartilage, the surface has fewer components which interfere with the bonding by surgical glues. The surgical glue appears to diffuse better into the treated cartilage tissue to form a stronger bond. In the preferred embodiment, the gelatinous matrix is removed from the cartilage before the surgical glue is applied to the cartilage surface.

Although illustrated hereinabove specifically for cartilage surface modification, it is contemplated that the present invention has application to in vivo surface modification of other joint-associated tissues such as bone, ligament and tendons, and other tissues as well. Thus, for example, the surface characteristics of tissues wetted with a biological fluid in vivo can be contacted with a compound or composition that forms a liquid crystalline or mesomorphic matrix with one or more components of the tissue surface or of the biological fluid, to modify the characteristics of the surface. Alternatively the matrix can be removed from the surface to provide a surface having a reduced amount and/or concentration of the tissue or fluid component forming the matrix.

EXAMPLES

Synovial fluid was obtained from bovine stifle joints (knee joints) within 30 minutes of sacrifice. The synovial fluid was aspirated from the joint using a 18-gauge needle with an attached syringe. All amino acids and poly-amino acids were purchased from Sigma Chemical Co. The water which was used to prepare reagent solutions and to rinse glass slides and substrates was purified by passage through a MILLI-Q® water purification system. Water thus obtained had a conductivity of about 18.2 MOhm cm.

The glass slides and glass substrates used in the following examples were cleaned by first immersing them in hot sulfuric acid bath for 10 minutes. The slides were rinsed thoroughly with purified water. Then they were placed in warm ammonium hydroxide:hydrogen peroxide (4:1 by volume) bath for 10 minutes. The slides were again rinsed with purified water.

Example 1

On a clean dry glass slide, poly-L-threonine (MW~12, 100), 0.5 mg dissolved in 0.1 ml of water was added to 0.05 to 0.3 ml of synovial fluid at room temperature. Prior to the addition of poly-threonine there was no observable liquid crystalline order in the synovial fluid under the optical microscope using polarized light. After the addition of the poly-L-threonine solution, there is almost an immediate gelation and liquid crystalline behavior as determined by observation of the gel with an optical microscope.

Example 2

Glass substrates, cleaned and prepared as mentioned above, were placed on a holder that exposed 4.84 cm$^2$ of area. A 3% by weight aqueous composition of various poly(amino acid) adhesive compositions was placed in this area and dried under vacuum. All samples were stored in a desiccator prior to mechanical testing.

Mechanical testing was done using the MINI44 INSTRON according to the following procedure (See FIG. 1). A 1 cm×1 cm piece of bovine cartilage (1) was cut from the articular cartilage surface of bovine knee or hip joints. One side of the cartilage piece was fixed to a glass slide with cyanoacrylate glue (2). The other side was treated either with poly(L-lysine) or poly-L-threonine. The synovial fluid or gelatinous matrix was not removed from any of the samples. A second glass slide was treated with a poly(amino acid) adhesive (3) and then pressed on the slide with the pretreated cartilage with a force of 5 Newtons for 5 minutes. The poly(amino acid) adhesives tested were: polyaspartic acid and lysine (wt ratio: 1:10); polyglutamic acid (80) and lysine (wt ratio: 1:12) and (wt ratio: 1:14); polyglutamic acid (80), lysine and alginate (wt ratio: 1:6:1); polyglutamic acid (80), lysine and polyglutamine (wt ratio: 1:6:1); polyglutamic acid (80), lysine, polyglutamine, and carboxymethyl cellulose (wt ratio: 1:6:1:1); polyglutamic acid (80), lysine, polyglutamine, and alginate (wt ratio: 1:6:1:1); and, polylysine, polyasparagine, and polyglutamine (wt ratio: 1:1:1).

Figure 2:
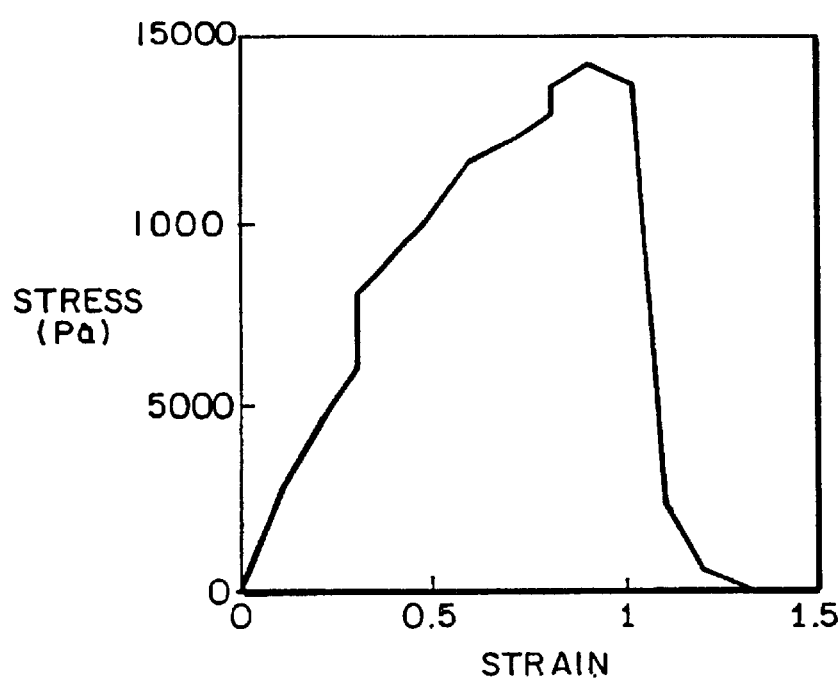

A pair of glass slides (4 and 5) was mounted in the INSTRON which utilized a separation speed of 0.50 mm per minute to pull the two slides apart. The stress was measured as the amount of force, in Pascals, necessary to separate the slides until the adhesive failed. The strain was measured as the maximum separation between the two slides just before the adhesive failed. Adhesive failure was determined by complete relief (i.e., 0 stress in Pascals) of the stress exhibited on the cartilage sample as determined by the MINI44 INSTRON. The typical appearance of the stress vs. strain curve is shown in FIG. 2.

TABLE 1

Adhesion Test on Cartilage with Synovial Fluid

| Adhesive* | poly-L-lysine pretreatment | | poly-L-threonine pretreatment | |
|---|---|---|---|---|
| | Stress (Pa) | Strain (mm) | Stress (Pa) | Strain (mm) |
| pAsp & Lys | 0 | 0 | 1200 | 1.0 |
| pGlu80 & Lys | 0 | 0 | 1000 | 2.0 |
| pGlu80 & Lys & Alg | 300 | 1.2 | 1400 | 1.2 |
| pGlu80 & Lys & Gln | 0 | 0 | 1100 | 1.2 |
| pGlu80 & Lys & Gln & CC | 200 | 1.0 | 1000 | 1.4 |
| pGlu80 & Lys & Gln & Alg | 100 | 1.0 | 950 | 1.0 |
| pLys & pAsn & Gln | 0 | 0 | 1150 | 1.0 |

*pAsn = poly-L-asparagine (mw 7900); pAsp = poly-L-aspartic acid (mw = 36,300); pGln = poly-L-glutamine (mw = 6300); pGlu80 = poly-L-glutamic acid (mw = 81500); pLys = poly-L-lysine (mw = 42000); CC = Carboxymethyl cellulose; Alg = Alginate;

Examination of the results from the adhesion tests of cartilage surfaces pretreated with either poly(L-lysine) or poly-L-threonine (see Table 1) revealed that for all poly (amino acid) adhesives tested, the cartilage which was pretreated with poly-L-threonine exhibited markedly improved bonding characteristics; it remained bonded to the poly(amino acid) adhesive under much greater stress force than the cartilage which was pretreated with poly(L-lysine). For the cartilage surfaces pretreated with poly(L-lysine) only, three out of the seven poly(amino acid) adhesives formed a bond with the cartilage surface. When the three poly(amino acid) adhesives that did bond to the poly-(L-lysine) pretreated cartilage were exposed to stress, they failed at much lower stress values than the corresponding poly-L-threonine pretreated cartilage.

Example 3

Glass substrates, cleaned and prepared as mentioned above, were placed on a holder that exposed 4.84 cm$^2$ of area. A 3% by weight aqueous composition of each of the poly(amino acids) adhesives is placed in this area and dried under vacuum. All samples are stored in a desiccator prior to mechanical testing.

A 1 cm×1 cm piece of bovine cartilage is cut from the articular cartilage surface of bovine knee or hip joints. One side of the cartilage piece is fixed to a glass slide with cyanoacrylate glue. The other side is treated with about 0.3 mg of poly-L-threonine. A gelatinous matrix forms on the cartilage surface. Blotting the cartilage surface with sterile gauze separates at least a portion of the gelatinous matrix from the cartilage surface.

After the removal of the gelatinous matrix, the cartilage surface is then prepared to accept the poly(amino acid) adhesives. The poly(amino acid) adhesives are: polyaspartic acid and lysine (wt ratio: 1:10); polyglutamic acid (80) and lysine (wt ratio: 1:12) and (wt ratio: 1:14); polyglutamic acid (80), lysine and alginate (wt ratio: 1:6:1); polyglutamic acid (80), lysine and polyglutamine (wt ratio: 1:6:1); polyglutamic acid (80), lysine, polyglutamine, and carboxymethyl cellulose (wt ratio: 1:6:1:1:); polyglutamic acid (80), lysine, polyglutamine, and alginate (wt ratio: 1:6:1:1); and, polylysine, polyasparagine, and polyglutamine (wt ratio: 1:1:1). The efficacy of bonding of surgical glues to the cartilage surface is further increased when the gelatinous matrix is removed from the cartilage surface.

What is claimed is:

1. A composition comprising a poly(hydroxy substituted amino acid) and synovial fluid, wherein the poly(hydroxy substituted amino acid) is selected from the group consisting of homopolymers, copolymers, terpolymers, and block copolymers of polythreonine, polyserine, polytyrosine, poly(hydroxyproline), and poly-5-hydroxy lysine.

2. The composition of claim 1 wherein the poly(hydroxy substituted amino acid) comprises polythreonine.

3. A method for removing synovial fluid from a cartilage surface comprising the steps of:

contacting said cartilage surface and said synovial fluid with a poly(hydroxy substituted amino acid) in an amount effective to form a liquid crystalline gel on said cartilage surface; and separating said liquid crystalline gel from said cartilage surface, wherein the poly(hydroxy substituted amino acid) is selected from the group consisting of homopolymers, copolymers, terpolymers, and block copolymers of polythreonine, polyserine, polytyrosine, poly(hydroxyproline), and poly-5-hydroxy lysine.

4. The method in claim 3 wherein the poly(hydroxy substituted amino acid) comprises polythreonine.

5. A method for removing synovial fluid from a surface of joint tissue, said tissue selected from a group consisting of cartilage, tendon, ligament or bone, said method comprising the steps of:

contacting said surface and said synovial fluid wit a poly(hydroxy substituted amino acid) in an amount effective to form a liquid crystalline or mesomorphic matrix on said surface, wherein the poly(hydroxy substituted amino acid) is selected from the group consisting of homopolymers, copolymers, terpolymers, and block copolymers of polythreoe, polyserine, polytyrosine, poly(hydroxyproline), and poly-5-hydroxy lysine; and separating said liquid crystalline or mesomorphic matrix from said surface.

6. The method in claim 5 wherein said tissue is cartilage tissue.

7. The method in claim 5 wherein said poly(hydroxy substituted amino acid) comprises polythreonine.

8. The composition of claim 1 wherein the poly(hydroxy substituted amino acid) is selected from the group consisting of homopolymers of polythreonine, polyserine, polytyrosine, poly(hydroxyproline), and poly-5-hydroxy lysine.

9. The method of claim 3 wherein the poly(hydroxy substituted amino acid) is selected from the group consisting of homopolymers of polythreonine, polyserine, polytytosine, poly(hydroxyproline), and poly-5-hydroxy lysine.

10. The method of claim 5 wherein the poly(hydroxy substituted amino acid) is selected from the group consisting of homopolymers of polythreonine, polyserine, polytyrosine, poly(hydroxyproline), and poly-5-hydroxy lysine.

11. A composition comprising polythreonine and synovial fluid.

12. A method for removing synovial fluid from a cartilage surface comprising the steps of:

contacting said cartilage surface and said synovial fluid with polythreonine in an amount effective to form a liquid crystalline gel on said cartilage surface; and separating said liquid crystalline gel from said cartilage surface.

13. A method for removing synovial fluid from a surface of joint tissue, said tissue selected from a group consisting of cartilage, tendon, ligament or bone, said method comprising the steps of:

contacting said surface and said synovial fluid with polythreonine in an amount effective to form a liquid crystalline or mesomorphic matrix on said surface; and separating said liquid crystalline or mesomorphic matrix from said surface.

14. The method of claim 13 wherein said tissue is cartilage tissue.

* * * * *

UNITED STATES PATENT AND TRADEMARK OFFICE
CERTIFICATE OF CORRECTION

PATENT NO. : 6,420,519 B1
DATED : July 16, 2002
INVENTOR(S) : Julia Hwang and Samuel I. Stupp It is certified that error appears in the above-identified patent and that said Letters Patent is hereby corrected as shown below:

Column 7,
Line 38, change "wit" to -- with --
Line 44, change "polythreoe" to -- polythreonine --

Column 8,
Line 16, change "polytytosine" to -- polytyrosine --

Signed and Sealed this

Eleventh Day of March, 2003

JAMES E. ROGAN
*Director of the United States Patent and Trademark Office*